United States Patent [19]
Kerr et al.

[11] Patent Number: 5,354,684
[45] Date of Patent: Oct. 11, 1994

[54] AGROBACTERIUM RADIOBACTER K84 CARRYING TRANSFER-DEFICIENT PAGK84 PLASMIDS

[75] Inventors: Allen Kerr, Adelaide; David A. Jones, Surrey Downs; Bruce G. Clare, Glenunga; Maarten H. Ryder, Brompton, all of Australia; Stephen K. Farrand, Seymour, Ill.

[73] Assignee: Luminis Pty. Ltd., Adelaide, Australia

[21] Appl. No.: 890,393

[22] Filed: May 26, 1992

Related U.S. Application Data

[63] Continuation of Ser. No. 260,451, Oct. 20, 1988, abandoned.

[30] Foreign Application Priority Data

Oct. 20, 1987 [AU] Australia ................... PI4977

[51] Int. Cl.$^5$ .................. C12N 1/21; C12N 15/74
[52] U.S. Cl. .................. 435/252.3; 435/320.1
[58] Field of Search .......... 435/71.3, 69.1, 320.1, 435/252.3

[56] References Cited

FOREIGN PATENT DOCUMENTS

| | | |
|---|---|---|
| 142924 | 5/1985 | European Pat. Off. |
| 157253 | 10/1985 | European Pat. Off. |
| 174166 | 3/1986 | European Pat. Off. |
| WO84/03298 | 8/1984 | PCT Int'l Appl. |

OTHER PUBLICATIONS

Ellis et al. (1979) Physiol. Plant Pathol. 15:311–319.
Shim et al. Phytopathology. 1987. vol. 77(3):463–6. Abstract.
Comai et al. Plasmid. 1983. vol. 10:21–30.
Farrand et al. 1985. Plasmid vol. 13:106–117.
Slota et al. 1982. Plasmid vol. 8:175–186.
Ryder et al. 1987. J. of Bact. vol. 169:4184–4189.
*Daniel McAlpine Memorial Lecture; Agrobacterium: pathogen, genetic engineer and biological control agent;* The Australasian Plant Pathology, vol. 16(3) 1987.
*Construction of a Tra deletion mutual of pAgK84 to safeguard the biological control of crown gall;* The Jones et al reference (Mol. Gen. Genet.) (1988)
Biological Abstracts vol. 80, No. 2, Abstract No. 12493.
*Genetic identification of functions of TL–DNA transcripts in octopine crown galls;* The Leemans et al reference (The EMBO Journal vol. 1, pp. 147–152, 1982).
*Intergeneric transfer and exchange recombination of restriction fragments cloned in pBR322: a novel strategy for the reversed genetics of the Ti plasmids of Agrobacterium Tumefaciens;* The Haute et al reference (The EMBO Journal vol. 2, No. 3, pp. 411–417, 1983).
Chem. Abstracts vol. 106, 1987, Abstract 106:132408f.
Chem. Abstracts vol. 106, 1987, Abstract 106:191012v.
Chem. Abstracts vol. 107 1987, Abstract 107:169607s.

Primary Examiner—Richard A. Schwartz
Assistant Examiner—Kathleen L. Choi
Attorney, Agent, or Firm—Merchant, Gould, Smith Edell, Welter & Schmidt

[57] ABSTRACT

The present invention provides transfer-deficient pAgK84 plasmids, non-pathogenic strains of *Agrobacterium radiobacter* K84 carrying such plasmids, and a method useful for control of crown gall disease mediated by *A. tumefaciens*. The plasmids include genes encoding the synthesis of the antibiotic agrocin 84 and are modified in the transfer region of the plasmid by sufficient deletion to inhibit transfer of the plasmid. The plasmids are used to develop non-pathogenic strains of *A. radiobacter* K84 that stably produce agrocin 84 and inhibit the development of crown gall disease.

4 Claims, 6 Drawing Sheets

AGROBACTERIUM RADIOBACTER K84 CARRYING TRANSFER-DEFICIENT PAGK84 PLASMIDS

This is a continuation, of application Ser. No. 07/260,451, filed Oct. 20, 1988, now abandoned.

The present invention relates to a mutant strain of *Agribacterium radiobacter* K84 and to a method of control of plant disease utilising same.

*Agrobacterium radiobacter* K84 is a non-pathogenic soil inhabiting bacterium used commercially for the biological control of crown gall which is a plant disease caused by the *Agrobacteium radiobacter* variety *tumefaciens*, a bacterium that lives in the soil. The bacterium enters plants through wounds and induces unregulated cell division leading to massive gall formation.

In Australia almond, peach and rose are crops most severely affected by crown gall. Until recently, satisfactory control of crown gall could be achieved by dipping the planting material of crops in a cell suspension of *Aqrobacterium radiobacter* K84. It has been found that *Agrobacterium radiobacter* K84 functions by the synthesis of agrocin 84, an antiobiotic responsible for the control of *A. tumefaciens*.

As effective as the agrocin control system has been, failures in field control have occurred. There have been recent reports of the acquisition, by sensitive strains, of a plasmid pAgK84, which contains genes encoding for the synthesis of and immunity to the agrocin 84 antibiotic. This can give rise to fully tumorigenic agrocin 84-resistant strains. This is also consistent with other reports that pAgK84 is transmissible to other agrobacteria apparently by plasmid mobilization and transfer. These failures may constitute a significant threat to the continued success of the biological control of crown gall.

It is accordingly an object of the present invention to overcome, or at least alleviate, one or more of the difficulties related to the prior art.

Accordingly, in a first aspect of the present invention there is provided a plasmid including genes encoding the synthesis of the antibiotic, agrocin 84, and modified to prevent transfer by a defined deletion in the transfer region.

The plasmid may be a derivative of the plasmid pAgK84. The plasmid may be characterised in that the Eco R1 fragments D1 and H are substantially completely removed therefrom. A restriction map of plasmid pAgK84 is provided in FIG. 1 hereto.

Accordingly, in a preferred aspect of the present invention there is provided a plasmid pAgK1026, which is pAgK84 Δ Eco R1 D1+H, as hereinafter described, and derivatives thereof.

In a further aspect of the present invention there is provided a non-pathogenic strain of *Agrobacterium radiobacter* K84 including a plasmid including genes encoding the synthesis of the antibiotic agrocin 84 modified to prevent transfer by deletion in the transfer region; derivatives thereof and mutants thereof.

It will be understood that such a strain may be a suitable candidate for the biological control of the plant disease crown gall. Such a strain maintains all the characteristics of the *Aqrobacterium radiobacter* strain K84, save for the fact that a substantial section of the transfer region has been deleted. Thus, the possibility of sensitive strains developing immunity via transmission of the plasmid pAgK84 apparently by plasmid mobilization and transfer is reduced or eliminated.

In a preferred form, the non-pathogenic strain of *Aqrobacterium radiobacter* K84 includes a plasmid which is a derivative of plasmid pAgK84.

Thus, in a preferred form there is provided a non-pathogenic strain of *Agrobacterium radiobacter* K84, strain K1026, derivatives thereof and mutants thereof as hereinafter described, a sample of which is maintained in the Culture Collection of the Plant Pathology Department, University of Adelaide, South Australia, Australia.

In a still further aspect of the present invention there is provided a method of preparing a plasmid including genes encoding the synthesis of the antibiotic, agrocin 84, modified to prevent transfer by deletion in the transfer region, which method includes providing
a plasmid pAgK84;
a suitable plasmid cloning vector;
inserting the Bam H1 fragment B1 of plasmid pAgK84 into the plasmid cloning vector, and
contacting the inserted fragment with the restriction enzyme Eco R1 to delete the Eco R1 fragements D1 and H.

A suitable plasmid cloning vector is plasmid pBR325. The plasmid formed when the Eco R1 fragments D1 and H are removed from the Bam H1 fragment B1 may be designated plasmid pMHR100 a sample of which is maintained in the Culture Collection of the Plant Pathology Department, University of Adelaide. The plasmid pMHR100 is characterised in that approximately 3.7 kb and 0.5 kb of plasmid pAgK84 are left on either side of the deletion. Accordingly, in a preferred aspect of the present invention there is provided the plasmid pMHR100; and derivatives thereof.

In order to provide a fragment of suitable size for later insertion, the 0.5 kb portion of pAgK84 on one side of the deletion may be increased to approximately 3.3 kb by adding the Eco R1 fragment D2 from a clone of Bam H1 fragment C of pAgK84.

Accordingly in a further aspect of the present invention the method may further include providing a plasmid including a Bam H1 fragment C of pAgK84 and adding the Eco R1 fragment D2 to the approximate 0.5 kb portion of pAgK84 remaining on one side of the deletion such that the portion remaining is increased to approximately 3.3 kb.

A suitable clone is that designated plasmid pDAJ101 and maintained in the culture collection maintained by the Plant Pathology Department, University of Adelaide, South Australia, Australia. The combined clone has been designated by the designation pDAJ102 a sample of which is maintained in the Culture Collection of the Plant Pathology Department, University of Adelaide. Accordingly, in a further preferred aspect of the present invention there is provided the plasmid pDAJ102.

The method of preparing a plasmid according to this aspect of the present invention may further include providing a first *Agrobacterium* strain harbouring the plasmid pAgK84 including an antiobiotic resistance marker inserted proximate the transfer region;
a second *Aqrobacterium radiobacter* K84 strain lacking the plasmid pAgK84, and
an Escherichia coli strain harbouring a plasmid cloning vector, pBR325, containing the transfer region of pAgK84 modified to prevent transfer by a defined deletion in the transfer region, mobilising and transferring the plasmid cloning vector including genes encoding the synthesis of the antibiotic, agrocin 84, modified by deletion of the Eco R1 fragments D1 and H into the antibiotic resistance marker strain and transferring the cointegrate by conjugation to the Agrobacterium radiobacter K84 strain lacking the plasmid pAgK84.

The method according to this aspect of the present invention may further include subjecting the transconjugant to a deletion-marker exchange.

The first Agrobacerium radoiobacter strain may include a Tn5 insertion just outside the Tra region. Such an insertion provides kanamycin resistance which may function as an antibiotic marker. An Agrobacterium strain C58NT1 strain may be used.

It will be understood that the resulting Tra− plasmid is stable in the strain so formed and shows normal agrocin 84 production.

The plasmid so formed has been designated by the designation pAgK1026, which is pAgK84 Δ Eco R1 D1+H. The Agrobacterium radiobacter K84 strain harbouring said antibiotic resistance has been designated by the designation strain K1026, a sample of which was deposited on Apr. on 4, 1987 and is maintained in the Culture Collection of the Plant Pathology Department, University of Adelaide.

As stated above, the Agrobacterium radiobacter K84 strain modified to prevent transfer may be utilised in the control of crown gall disease in plants. Accordingly in a still further aspect of the present invention, there is provided a method for the control of crown gall disease in plants which method includes providing
a plant material to be treated;
a non-pathogenic strain of Agrobacterium radiobacter K84 including a plasmid including genes encoding the synthesis of agrocin 84, modified to prevent transfer by deletion in the transfer region;
contacting the plant material directly or indirectly with the non-pathogenic Agrobacterium radiocater K84 strain.

The plant material to be treated include seeds, seedlings, growing crops. The crops may be of any suitable type and may include stone fruit trees, Prunus species, cane berries, euonymus, clematis and persimmon. Almond, pecan, walnut, boysenberry and raspberry, stone fruit including peach, cherry, plum and apricot, and rose trees are particularly preferred.

The plant material may be contacted with the Agrobacterium radiobacter K84 strain by applying the plant material into a cell suspension of the strain.

The Agrobacterium radiobacter K84 strain may be the strain K1026, as described above.

The present invention will now be more fully described with reference to the following examples and drawings. It should be understood, however, that the description following is illustrative only and should not be taken in any way as a restriction on the generality of the invention described above.

In the figures:

FIG. 1 is a Bam H1 and Eco R1 restriction map of pagK84 showing the transfer, agrocin synthesis and agrocin immunity regions.

FIG. 2 illustrates steps in the construction of intermediate plasmid pDAJ102 containing a deletion overlapping the Tra region. B and E symbolize Bam H1 and Eco R1 ends of the inserts, respectively. E is also used to indicate the Eco R1 site in the Cm gene.

FIG. 3 illustrates the construction of pAgK1026. For illustrative purposes the homologous recombination events leading to deletion-marker exchange are shown occurring firstly in Eco R1 fragment D2, to form a cointegrate, and then later in Eco R1 fragment B or F, to resolve it, but they could also have occurred in the reverse order.

FIG. 4 illustrates Eco R1 digests of plasmids involved in the construction of pAgK1026. Fragments were separated by electrophoresis for 3 h at 100 V in a 0.7% agarose gel. Lanes 1 and 8 contain lambda phage DNA digested with HindIII; lane 2, pAgK84 from strain K84; lane 3, pAgK84::Tn5A28 from strain A28; lane 4, pDAJ102 from strain K1023; lane 4, pAgK84::Tn5A28::pDAJ102 from strain K1024; lane 6, pAgK84::Tn5A28::pDAJ102 from strain K1025; lane 7, pAgK1026 from strain K1026. Lanes 2, 6, 7 also contain a background of restriction fragments derived from pAtK84b. bands A–C contain Eco R1 fragments A–C of pAgK84; band D, Eco R1 fragments A–C of pAgK84 in lane 2 but only D2 in lanes 3–7; bands E–K, Eco R1 fragments E–K of pAgK84; band L, Eco R1 fragment D1 of pAgK84 containing Tn5 which has no Eco R1 sites; band M, an Eco R1 fragment containing the large Eco R1-BamH1 fragment of pBR325 joined via a Bam H1 site to the part of Eco R1 fragment B contained within Bam H1 fragment B1 of pAgK84.

FIG. 5 illustrates the plasmids contained within Agrobacterium strains K84, K434 and K1026. Undigested plasmids were separated by electrophoresis for 3 h at 100 V in a 0.7% agarose gel. Lanes 1 and 5 contain undigested lambda phage DNA; lane 2, plasmids from strain K84; lane 3, plasmids from strain K434; lane 4, plasmids from strain K1026. Band A contains the cryptic plasmid; band B, pAtK84b, the nopaline catabolizing plasmid; band C, pAgK84; band D, pAgK1026.

EXAMPLE

Construction of a transfer deficient deletion mutant of pAgK84

Figure 1:
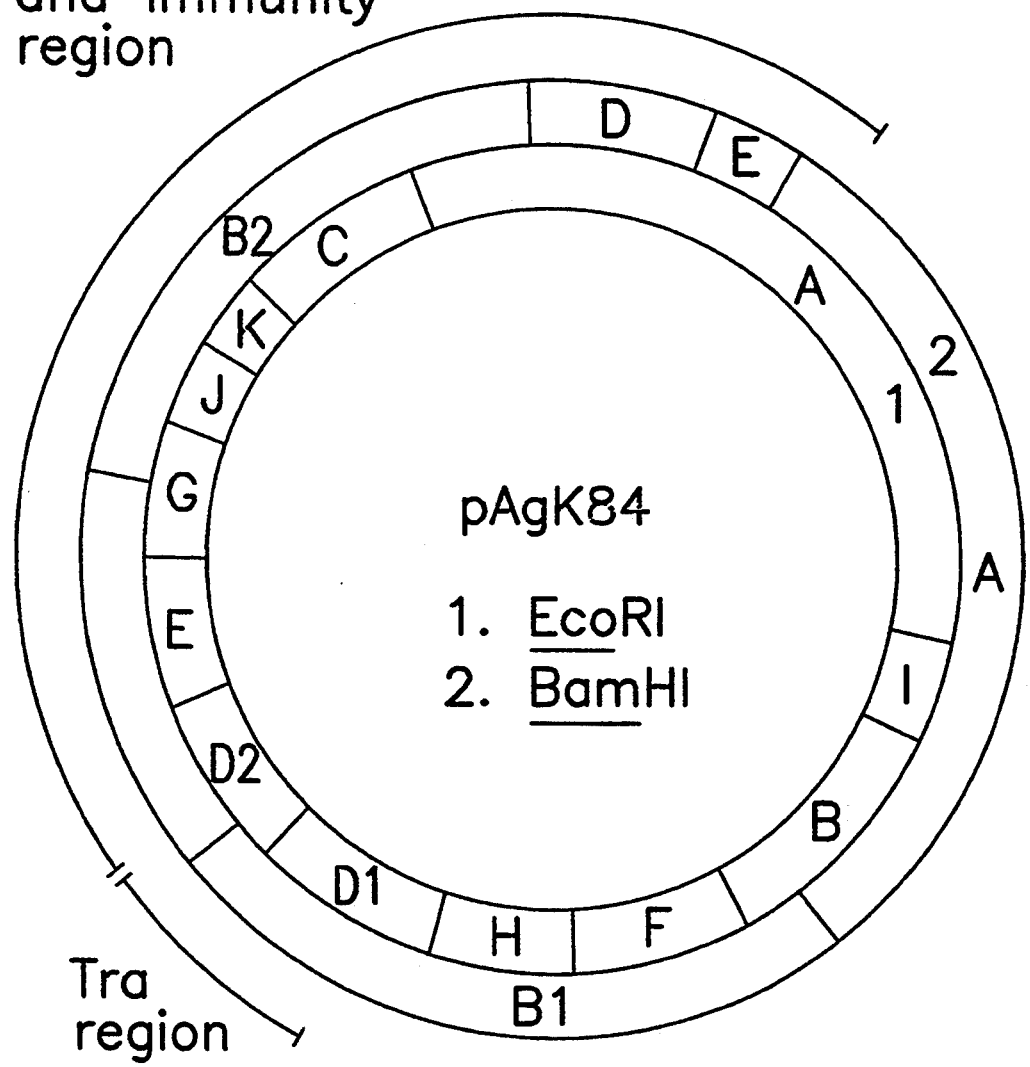
Figure 2:
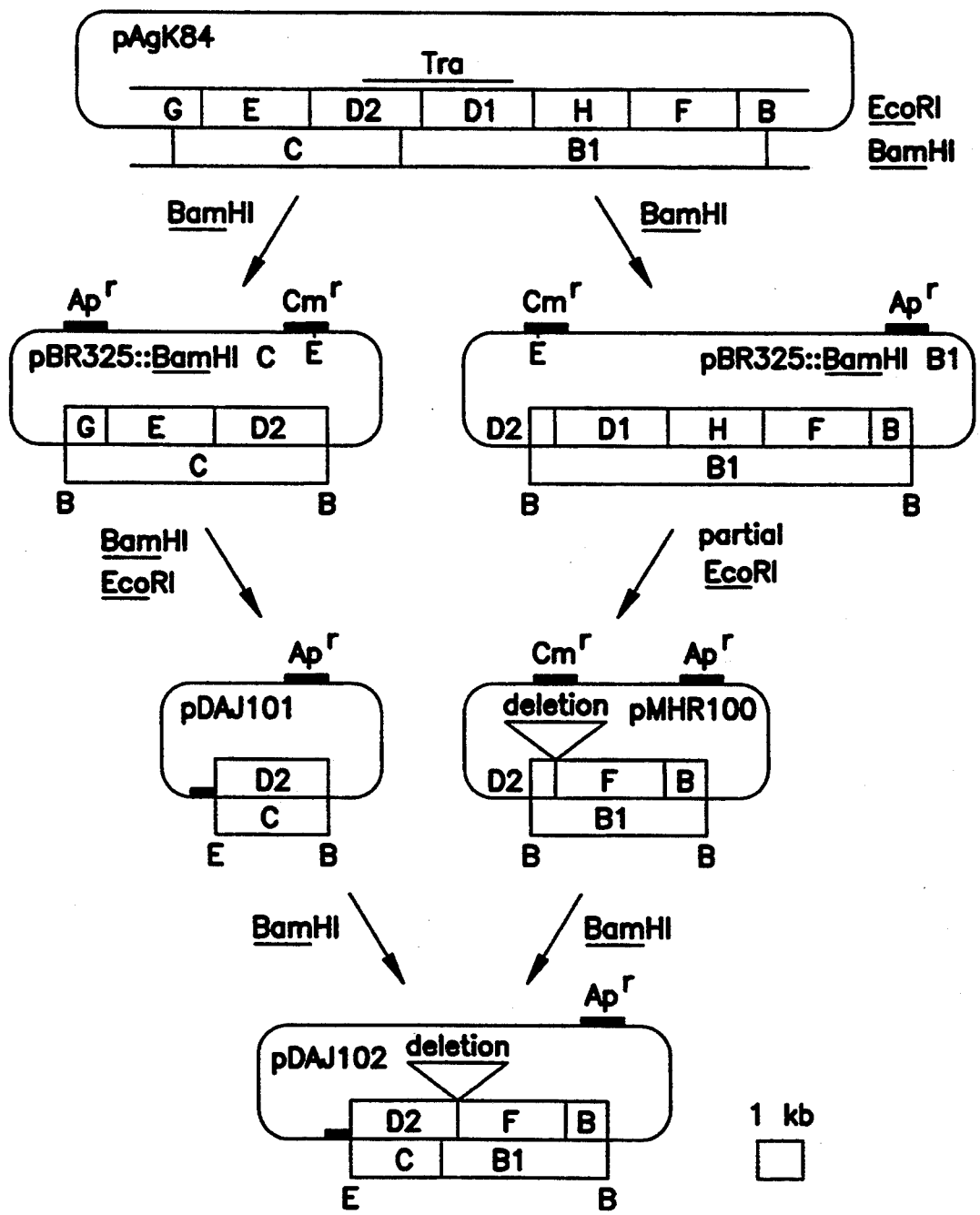

A BamH1 library of pAgK84 was prepared by ligating BamH1 digested fragments of pAgK84 into pBR325 which had been cut with BamH1, and transforming into E. coli HB101. Transformants were recovered by selection on LB agar for resistance to 40 ug/ml ampicillin (Ap) and 25 ug/ml chloramphenicol (Cm), and by screening on LB agar for sensitivity to 10 ug/ml tetracycline (Tc), since cloning into the BamH1 site of pBR325 inactivates the tetracycline resistance gene. Two clones, pBR325::BamH1 B1 (in strain K840) and pBR325::BamH1 C (in strain K1008) (FIG. 2), which overlap the Tra region of pAgK84 were identified by single and double digests of plasmid minipreparations with BamH1, EcoR1 and Sma1.

To generate a deletion, 4 ug of pBR325::BamH1 B1 DNA was partially digested for 1 hr with 1 unit of EcoR1, and after checking the digestion by agarose gel electrophoresis, 1.5 ug was religated, from which 0.15 ug was used for transformation into *E. coli* HB101. Transformants were selected on LB agar for resistance to 25 ug/ml Cm, to ensure that deletions involving the EcoR1 site of pBR325, which is in the chloramphenicol resistance gene, were not recovered. Transformants were screened for the loss of EcoR1 fragments by agarose gel electrophoresis of plasmid minipreparations digested with EcoR1. One deletion derivative, pHMR100 (in strain K1007) (FIG. 2), lacked the contiguous EcoR1 fragments D1 and H, a total of 5.9 kb, but retained EcoR1 fragment F and the part of EcoR1 fragment B contained within BamH1 fragment B1, a total of 3.7 kb, on one side of the deletion, and the part of EcoR1 fragment D2 contained within BamH1 fragment B1, 0.5 kb, on the other, as confirmed by agarose gel electrophoresis of single and double digests of plasmid minipreparations with BamH1, EcoR1 and Sma1. The 0.5 kb portion of EcoR1 fragment D2 proved insufficient to allow deletion-marker exchange by homologous recombination, so it was increased to 3.3 kb by adding the remainder of EcoR1 fragment D2 from pBR325;;BamH1 C. as described below.

pBR325::BamH1 C was cut with BamH1 and EcoR1 to generate five fragments which were separated by agarose gel electrophoresis. The 4.4 kb fragment, which contains the majority of pBR325 i.e. from the BamH1 site in the tetracycline resistance gene to the EcoR1 site in the chloramphenicol resistance gene, and the 2.8 kb fragment, which was the part of EcoR1 fragment D2 contained within BamH1 fragment C, were recovered. The 4.4 kb fragment was treated with phosphatase, ligated to the 2.8 kb fragment and transformed into *E. coli* HB101. Transformants were selected on LB agar for resistance to 40 ug/ml Ap and the identity of the resultant plasmid, pDAJ101 (in strain K1022) (FIG. 2), was confirmed by agarose gel electrophoresis of single and double digests of plasmid minipreparations with BamH1 and EcoR1.

pMHR100 was then cut with BamH1 to generate 2 fragments which were separated by agarose gel electrophoresis. The 4.2 kb BamH1 fragment B1 bearing the deletion, was recovered, ligated to pDAJ101 which had been cut with BamH1 and treated with phosphatase, and transformed into HB101. Transformants were selected on LB agar for resistance to 40 ug/ml Ap and the orientation of the BamH1 fragment B1 insert was checked by agarose gel electrophoresis of plasmid minipreparations digested with EcoR1. This generated pDAJ102 (in strain K1023) (FIG. 2) which, having reconstituted the EcoR1 fragment D2, carried sufficient DNA on either side of the deletion to allow deletion-marker exchange by homologous recombination.

pDAJ102 was conjugatively transferred from *E. coli* into Agrobacterium strain A28 carrying pAgK84::Tn5A28 by triparental mating. Strain K1024, a transconjugant bearing the cointegrate pAgK84::Tn5A28::pDAJ102 (FIG. 3) formed by homologous recombination, was recovered on YMA, on which the *E. coli* donor and helper strains cannot grow, by selection for resistance to 100 ug/ml carbenicillin (Cb) and 50 ug/ml kanamycin (Km), and checked for the presence of the cointegrate by agarose gel electrophoresis of plasmid minipreparations digested with EcoR1. The A28 Tn5 insertion lies inside the region covered by the deletion but just outside of the Tra region (FIG. 3), so the cointegrate was Tra+.

The cointegrate was conjugatively transferred to Agrobacterium strain K434 in a biparental mating Strain K1025, a transconjugant containing the cointegrate, was recovered on Bergerson's medium containing 0.2% sodium tartrate, on which the biovar 2 recipient could grow but the biovar 1 donor could not, by selection for resistance to 200 ug/ml Km, and checked for the presence of the cointegrate by agarose gel electrophoresis of undigested and EcoR1 digested plasmid minipreparations. Strain K1025 was grown non-selectively in liquid YEB for 3 subcultures prior to plating on YEB agar at a colony density of ca. 150–200 colonies/plate followed by replica plating onto YEB agar and YEB agar containing 200 ug/ml Km. Strain K1026, a spontaneous kanamycin sensitive derivative of strain K1025, which had resolved the cointegrate by homologous recombination to generate a deletion-marker exchange (FIG. 3), was recovered as a single occurrence among ca. 7000 colonies replicated. The identity of pAgK1026, which is pAgK84 EcoR1D1 +H in strain K1026 was confirmed by agarose gel electrophoresis of plasmid minipreparations digested with EcoR1.

Figure 4:
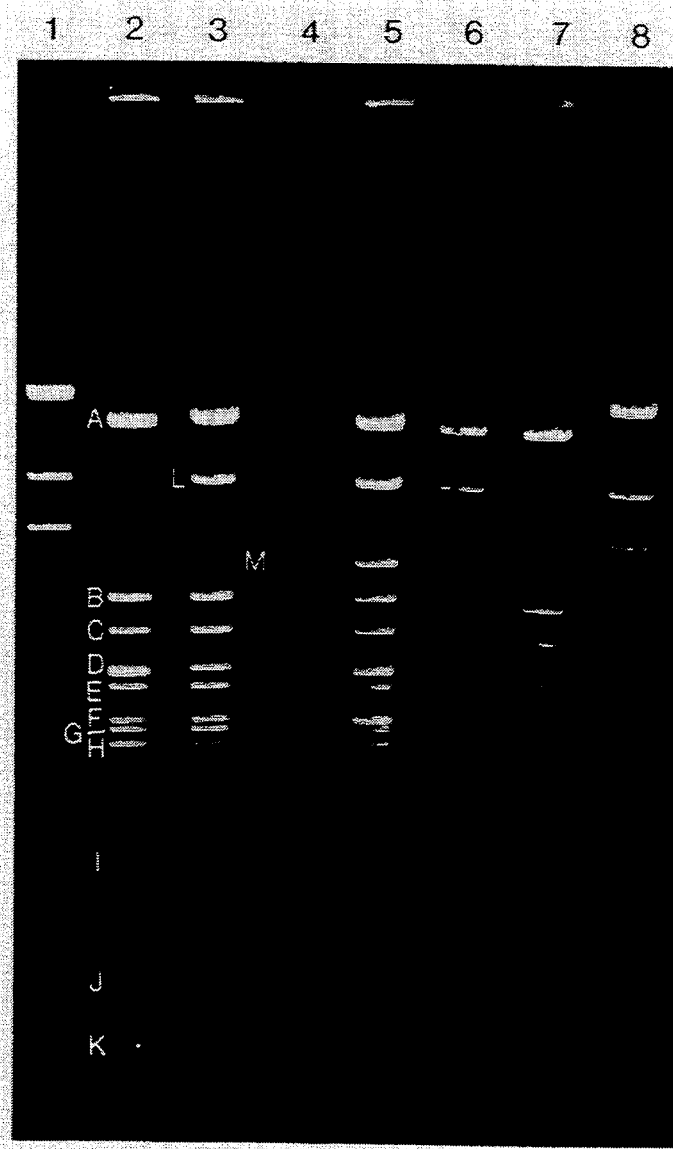
Figure 5:
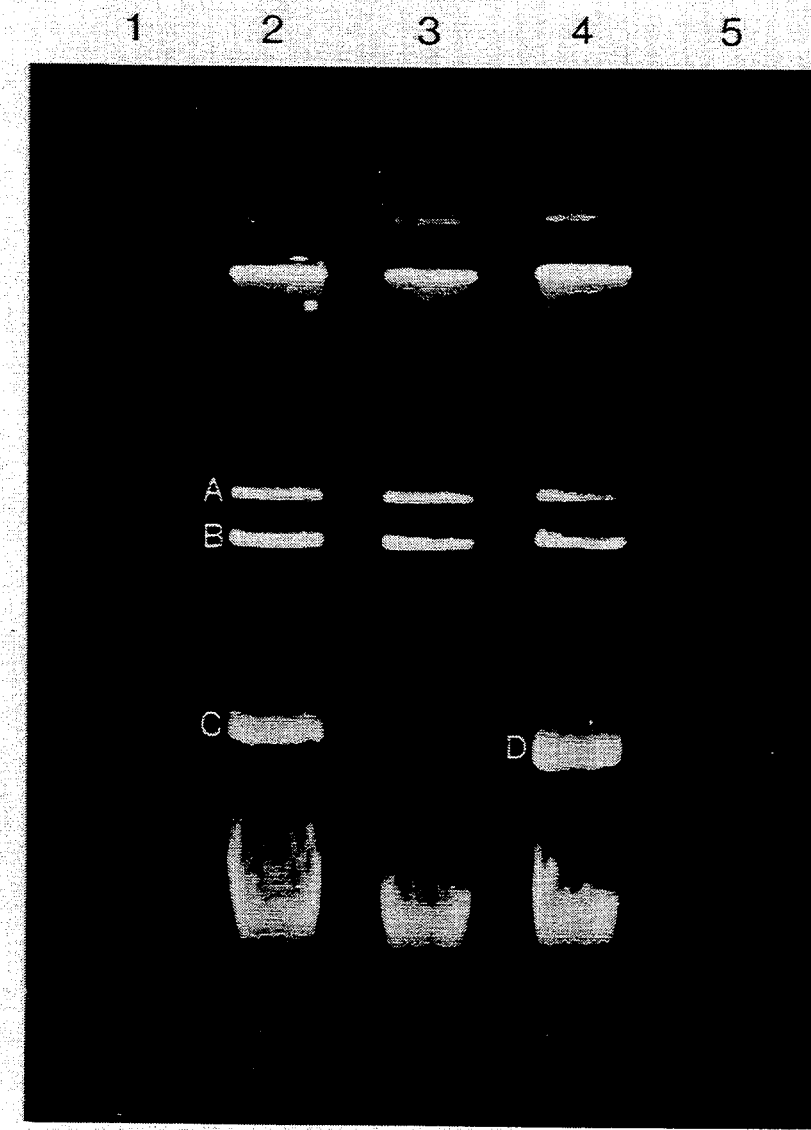

The identity of the mutant plasmid, designated pAgK1026, in strain K1026 was confirmed by analysis of Eco R1 digested (FIG. 4) and undigested (FIG. 5) plasmid mini-preparations. The latter also confirmed retention of the plasmid complement of strain K84 by strain K1026.

The complete loss of vector and Tn5 sequences from strain K1026 may be inferred by the loss of Cb resistance carried by the vector and Km and streptomycin (Sm) resistance carried by Tn5. This indicates that no foreign DNA remains in strain K1026.

Figure 6:
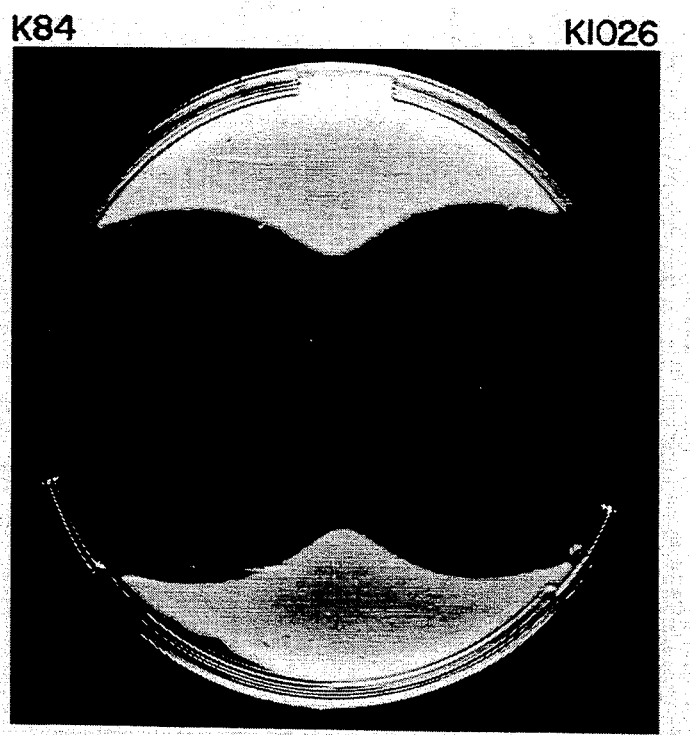
FIG. 6 illustrates the bioassay for the production of agrocin 84 by Agrobacterium strains K84 and K1026. Agrocin production is indicated by the zones of inhibition in the growth of the strain K198 overlay on Stonier's medium.

Strains K84 and K1026 were tested for agrocin 84 production using equivalent cell numbers of the two strains in order to semi-quantify the amount of agrocin produced. Strain K1026 produces agrocin 84 (FIG. 6) indicating that pAgK1026 retains the agrocin 84 biosynthetic capacity of its pAgK84 progenitor. Furthermore, the sizes of the inhibition zones for strains K84 and K1026 were similar (FIG. 6) indicating that they produce similar amounts of agrocin 84. This provides indirect evidence that pAgK1026 retains the copy number of its pAgK84 progenitor since Shim et al. (1987) found that a mutant of pAgK84 with increased copy number produced a correspondingly increased amount of agrocin 84.

To study plasmid stability and transfer ability, both pAgK84 and pAgK1026 were marked with the Cm and Cb genes of pBR325, as follows. pBR325::Bam H1C was transferred by triparental mating from strain K1008 to both strains K1026 and K84, where pBR325::Bam H1C formed a cointegrate with pAgK1026 and pAgK84, respectively, by homologous recombination. Transconjugant strains K1027, containing pAgK1026::pBR325::Bam H1 C, and K1028, containing pAgK84::pBR325::Bam H1 C, were recovered on YMA, on which the *E. coli* donor and helper strains could not grow, by selection for resistance to 100 ug/ml Cm and 500 ug/ml Cb, and checked for the presence of their respective cointegrates by analysis of Eco R1 digests (data not shown).

To assay for plasmid stability, strains K1027 and K1028 were subcultured non-selectively ten times, as described above, prior to plating on YEB agar at a colony density of ca. 40 colonies/plate. The resultant colonies were replica plated onto YEB agar and YEB agar containing 100 ug/ml Cm and 500 ug/ml Cb. For strain K1027, 28 colonies sensitive to Cm and/or Cb were recovered out of 1412 replica plated, giving 1.98% marker loss after ten subcultures. Similarly for strain K1028, 35 colonies sensitive to Cm and/or Cb were recovered out of 1834 replica plated, giving 1.91% marker loss after ten subcultures, which is not significantly different to that for strain K1027 ($P=0.87$). The antibiotic sensitive isolates were then assayed for agrocin 84 production and all were found to produce the antibiotic, indicating that they all had not lost their respective agrocin plasmids. They presumably lost their markers by resolution of the cointegrates, with the concomitant loss of pBR325::Bam H1 C which cannot replicate independently in Agrobacterium. Thus, there was no loss of pAgK1026 or pAgK84 after 10 subcultures, indicating that pAgK1026 retains the stability of its progenitor pAgK84.

Figure 7:
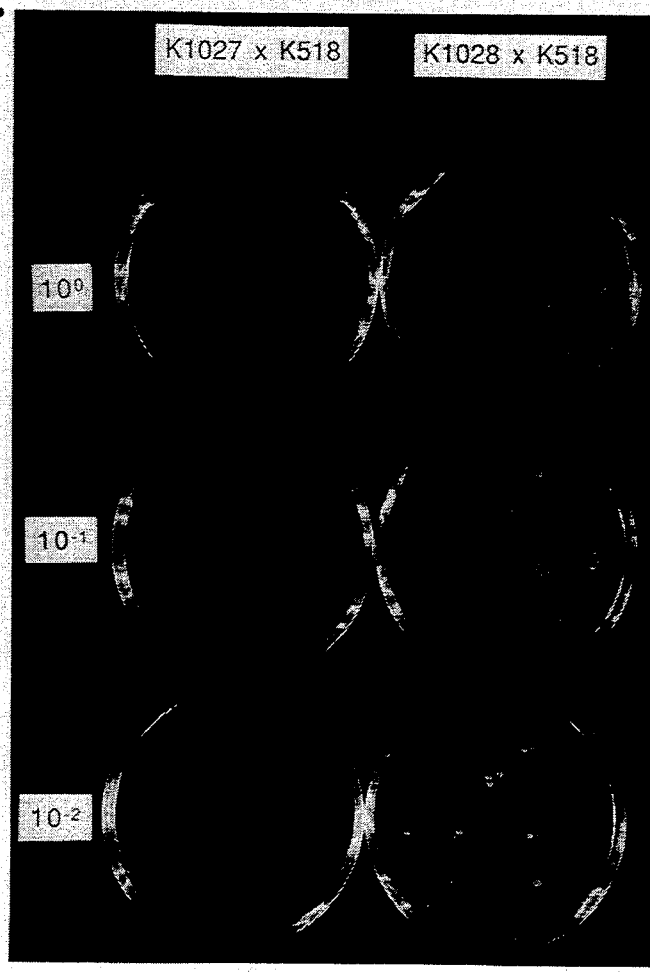
FIG. 7 illustrates the transfer ability of pAgK84 and its engineered deletion derivative, pAgK1026. Strain K1027, containing pAgK1026, and strain K1028, containing pAgK84, were mated with strain K518 and 10 ul droplets of a tenfold dilution series of the mating mixture were spotted onto media selecting for transconjugants.

To assay for plasmid transfer ability, strains K1027 and K1028 wre crossed to K518 in biparental droplet matings on Petit's agar containing 0.2% nopaline, as described in Materials and methods. Donor and recipient strains were able to grow on the mating medium because each harbours pAtK84b, a nopaline catabolizing plasmid. Numbers of donors were determined on NA containing 50 ug/ml Cm, numbers of recipients on NA containing 50 ug/ml refampicin (Rif), and numbers of transconjugants on NA containing 50 ug/ml Rif, 50 ug/ml Cm and 100 ug/ml Cb. No transconjugants were observed from the cross in which K1027 was the donor (FIG. 7). This gave transmission frequencies of $<3.84\times10^{-7}$ per donor and $<1.96\times10^{-8}$ per recipient. When K1028 was the donor many transconjugants were observed (FIG. 7), giving a transmission frequencies of $3.34\times10^{-4}$ per donor and $3.96\times10^{-5}$ per recipient. Clearly pAgK1026 is a Tra$^-$ mutant of pAgK84.

FIELD TRIALS

Materials and Methods

Preparation of bacteria

*A. radiobacter* biovar-2 strains K84 and K1026 were used to treat almond-seedling roots to prevent crown gall incited by *A. tumefaciens* biovar-2 strain K27 which is sensitive to agrocin 84. Prior to the pot trial, a fresh culture of K27 was subcultured onto ninety 10-ml Yeast Mannitol Agar (YMA) slopes in McCartney bottles, and fresh cultures of K84 and K1026 were subcultured onto 40-ml YMA slopes in 200-ml medicine flats. All cultures were grown for 3 days at 25 C.

Preparation of almond seedlings

Fresh almond seeds (cultivar Challeston) were then planted, one per pot, in 20-cm diameter pots containing UC potting mix and kept moist. Seedlings appeared 3-4 weeks later. One batch of seedlings was grown for 2 months and another for 10 months before the pot trial. Two days before the pot trial, seedling foliage was pruned severely to reduce stress due to transpirational water-loss after replanting.

Preparation of soil

Ninety 25-cm diameter pots were filled with a non-sterile sandy-loam, 10 kg per pot, over a 2 cm layer of pine-bark chips. Two days before replanting the treated almond-seedlings in this soil, the ninety 3-d cultures of K27 were each suspended in 500 ml of non-chlorinated water and poured into the soil, one culture per pot. The suspensions were then mixed into the top 10 cm of soil and watered in. The suspensions of K27 were estimated by optical density measurements to contain about $2\times10^7$ cells per ml, so, assuming uniform dispersal in the soil, the resultant concentration would have been approximately $10^6$ cells per g. The actual distribution of K27 in the soil was not examined.

Treatment of almond seedling

The 3 day cultures of K84 and K1026 were suspended in 5 L of non-chlorinated water. The suspensions were estimated by optical density measurements to contain about $10^7$ cells per ml. The almond seedlings were removed from their pots, the soil shaken gently from their roots, and the primary and lateral roots trimmed to a length of appproximately 20 cm. The plants were immersed for about 10 sec, to just above the crown, in either water or a suspension of K84 or K1026. They were then replanted, one per pot, in the soil infested previously with K27 and watered. The distribution of K84 or K1026 on the roots was not examined.

The plants were grown outdoors for 7 months, and a suitable fertilizer was applied at 6 week intervals, from June 1987 (early winter) to January 1988 (mid summer). They were then removed from their pots, the soil shaken gently from their roots, and the roots washed by repeated immersion in tap water. The number of galls on the roots was recorded for each plant.

Pot trial layout

The pot trial was set up with 15 replicates arranged in 15 rows of 6 plants. Each row was randomized with respect to the 6 combinations of the three treatments, water, K84 and K1026, and the two seedling-ages, 2 and 10 months. There was no space between rows or between pots within rows. No precautions were taken to prevent pot-to-pot spread of bacteria, and this did not appear to be a problem.

StatistiCal analysis

Because of the skewed and non-normal distribution of the data, even after transformation, parametric tests such as analysis of variance were inappropriate, so that data were analysed non-parametrically using the Kruskal-Wallis test. The Kruskal-Wallis test was applied separately to the 2 and 10 month seedlings and was used to compare all three treatments and to compare K84 and K1026 treatments.

Recovery of agrobacteria from roots and galls

Five grams of roots located within 10 cm of the crown were excised from each of five 10 month seedlings treated with K84 and similarly for K1026. Each root mass was placed in sterile double-distilled water, shaken vigorously, placed at 4C for 3 hr, and shaken vigorously once again. Dilutions of $10^{-1}$ and $10^{-2}$ in buffered saline were prepared and eighteen 10-ul droplets of each dilution were placed onto New and Kerr medium for isolation of Agrobacterium biovar-2. These plates were incubated for 4 days at 25C.

Five "healthy" 1 to 2-g galls from each of five 10 month seedlings treated with water were detached, immersed in 1.5% sodium hypochlorite for 2 min and then rinsed three times in sterile double-distilled water. The surface disinfected galls were then placed in 10 ml of sterile double-distilled water and macerated. The mixture was placed at 4C for 3 hours, shaken vigorously, and two loops full of the supernatant were streaked onto New and Kerr medium and the plates incubated as above. Similarly, eight "healthy" galls 0.75 g were sampled individually from seedlings treated with K84 or K1026.

All isolates recovered were streaked on New and Kerr medium and pure cultures, isolated from the resultant single colonies, were maintained on YMA slopes for use in subsequent tests.

Testing recovered agrobacteria for agrocin 84 production or sensitivity.

The method of Stonier, as modified by Kerr and Htay, was used for agrocin-84 bioassays. The recovered agrobacteria were tested for agrocin production by using them as producers in the agrocin bioassay with strain K198 used as the indicator. The latter is a biovar-1 strain of *A.tumefaciens* that harbours the same agrocin-sensitive Ti-plasmid as K27. Strains which did not produce agrocin were then tested for agrocin sensitivity by using them as indicators in the agrocin bioassay with K1026 used as the producer.

Testing recovered agrobacteria for pathogenicity on tomato seedlings

The recovered agrobacteria were tested for tumorigenicity by multiple stab-inoculations of 6 week tomato-seedlings (cultivar Rouge de Marmande). Inocula were prepared from 3-day cultures on YMA slopes. Two loops full of bacteria were removed and suspended in 1 ml of sterile distilled-water. A flame-sterilized needle was dipped into the suspensions and stabbed into the stems of the tomato plants, five time for each strain. The stems were assessed 6 weeks later for gall formation.

Plasmid content of recovered aqrobacteria

Mini-preparations of plasmids from the recovered agrobacteria were performed as described by Farrand et al. and plasmid content was characterised by agarose gel electrophoresis as described by Maniatis et al.

Results

Pot Trial

Galls were rare or absent on the roots of seedlings treated with K84 or K1026, but frequent on those treated with water (Table 1). The difference is so clear as to obviate the need for statistical confirmation. Nevertheless, Kruskal-Wallis tests were used to compare the three treatments and found to confirm a significant difference (H adjusted for ties=29.00 and 34.02 for 2 and 10 month seedlings, respectively, with $p<0.001$ in both cases). The similarity of K84 and K1026 treatments is also so clear as to obviate the need for statistical confirmation. Again nevertheless, Kruskal-Wallis tests were used to compare the two treatments and found to confirm the similarity (H adjusted for ties=0.41 and 0.35 for 2 and 10 month seedlings, respectively, with $0.5<p<0.7$ in both cases).

Recovered agrobacteria

Only agrocin-producing non-tumorigenic agrobacteria and agrocin-sensitive tumorigenic agrobacteria were recovered from the roots of K84 or K1026-treated plants (Table 2). All of the non-tumorigenic strains and a sample of the tumorigenic strains (five from each treatment) were analysed for plasmid content. K84 and K1026 each contain 3 plasmids, a large cryptic plasmid, pAtK84a, a smaller nopaline catabolic plasmid, pAtK84b, and a still smaller agrocin-84 plasmid, pAgK84 and pAgK1026, respectively, whereas K27 contains 2 plasmids, a cryptic plasmid pAtK27, slightly larger than pAtK84a, and a Ti plasmid pTiK27, intermediate in size to pAtK84a and pAtK84b. The plasmid analysis showed the non-tumorigenic strains to correspond to K84, if recovered from K84-treated plants, or K1026, if recovered from K1026-treated plants and the tumorigenic strains to correspond to K27 (data not shown). There was great variation between plants in the population ratio of K84 or K1026 to K27, but clearly there was an overall excess of K27 (Table 2).

Similarly, only K84 or K1026, and K27, were recovered from the few galls which occurred on the roots of K84 or K1026-treated plants (Table 2). There appeared to be a bimodal polarization in the population ratio of K84 or K1026 to K27, with 5 of the 8 galls containing almost all K84 or K1026 and 2 of the 8 galls containing almost all K27. In contrast, only K27 was recovered from galls on the roots of water-treated plants.

It is clear from the results of the pot trial that K1026 is as effective as K84 in controlling crown gall. It is also clear from the recovery data that relative to K84, K1026 has a similar ability to colonize and survive on roots as well as to colonize galls and displace inciting agrobacteria. Thus, K1026 appears to retain the ecological competence of its progenitor, K84.

It is interesting that there was an apparent bimodal polarization in the population ratios of K84 or K1026 to K27 in the few galls on K84 or K1026-treated plants. K84 and K1026 both utilize the opines nopaline and agrocinopine synthesized by K27-induced galls. So, consistent with the opine concept, those galls with an excess of K84 or K1026 presumably reflect K84 or K1026 colonization of these galls, with the concomitant displacement of K27, which, in the presence of agrocinopine, becomes more sensitive to agrocin 84. The galls in which there was an excess of K27 presumably reflect opportunities for colonization that were missed.

It is also interesting that neither K84 nor K1026 prevented co-colonization of the roots of K84 or K1026-treated plants by K27; and in fact there was an excess of K27 over K84 or K1026. Furthermore, very few galls were induced despite the excess of K27. This apparent anomaly, of inhibition of tumorigenesis without inhibition of root colonization and growth, is surprising.

TABLE 1

The effect of treating almond seedlings with water, a suspension of *Agrobacterium radiobacter* strain K84, or a suspension of *A.radiobacter* strain K1026, on grown gall induced by *A.tumefaciens* strain K27.

| Plant age | Treatment | No. plants surviving | % plants with galls | No. galls per plant | | |
|---|---|---|---|---|---|---|
| | | | | Mean | Median | Range |
| 2 mth | Water | 12 | 100 | 9.33 | 7.5 | 3–23 |
| | K84 | 14 | 14 | 0.21 | 0 | 0–2 |
| | K1026 | 12 | 25 | 0.33 | 0 | 0–2 |
| 10 mth | Water | 15 | 100 | 46.33 | 41 | 10–103 |
| | K84 | 15 | 20 | 0.20 | 0 | 0–1 |
| | K1026 | 15 | 27 | 0.67 | 0 | 0–5 |

TABLE 2

Numbers of agrobacteria recovered and characterized for agrocin production and sensitivity, and tumorigenicity, from the roots of 10-month almond-seedlings treated with K84 or K1026, and from galls on the roots of 10-month almond-seedlings treated with water, K84 or K1026.

| Source | Sample | Agrocin-producing non-tumorigenic (K84 or K1026) | Agrocin-sensitive tumorigenic (K27) |
|---|---|---|---|
| Roots of plants treated wth K84 | 1 | 0 | 9 |
| | 2 | 1 | 8 |
| | 3 | 5 | 7 |

TABLE 2-continued

Numbers of agrobacteria recovered and characterized for agrocin production and sensitivity, and tumorigenicity, from the roots of 10-month almond-seedlings treated with K84 or K1026, and from galls on the roots of 10-month almond-seedlings treated with water, K84 or K1026.

| Source | Sample | Agrocin-producing non-tumorigenic (K84 or K1026) | Agrocin-sensitive tumorigenic (K27) |
|---|---|---|---|
| | 4 | 1 | 10 |
| | 5 | 3 | 10 |
| Roots of plants treated with K1026 | 1 | 1 | 8 |
| | 2 | 0 | 9 |
| | 3 | 5 | 5 |
| | 4 | 10 | 0 |
| | 5 | 3 | 5 |
| Galls on the roots of plants treated with K84 | 1 | 1 | 9 |
| | 2 | 8 | 1 |
| Galls on the roots of plants treated with K1026 | 1 | 10 | 0 |
| | 2 | 10 | 0 |
| | 3 | 0 | 10 |
| | 4 | 10 | 0 |
| | 5 | 10 | 0 |
| | 6 | 6 | 4 |
| Galls on the roots of plants treated with water | 1-5 | 0 | 15 |

Finally, it is to be understood that various other modifications and/or alterations may be made without departing from the spirit of the present invention as outlined herein.

We claim:

1. A non-pathogenic strain of *Agrobacterium radiobacter* K84 comprising a stable modified plasmid pAgK84 including genes encoding the synthesis of the antibiotic agrocin 84 and also modified by a deletion of the EcoRI D1 fragment to inhibit transfer of the plasmid.

Figure 3:
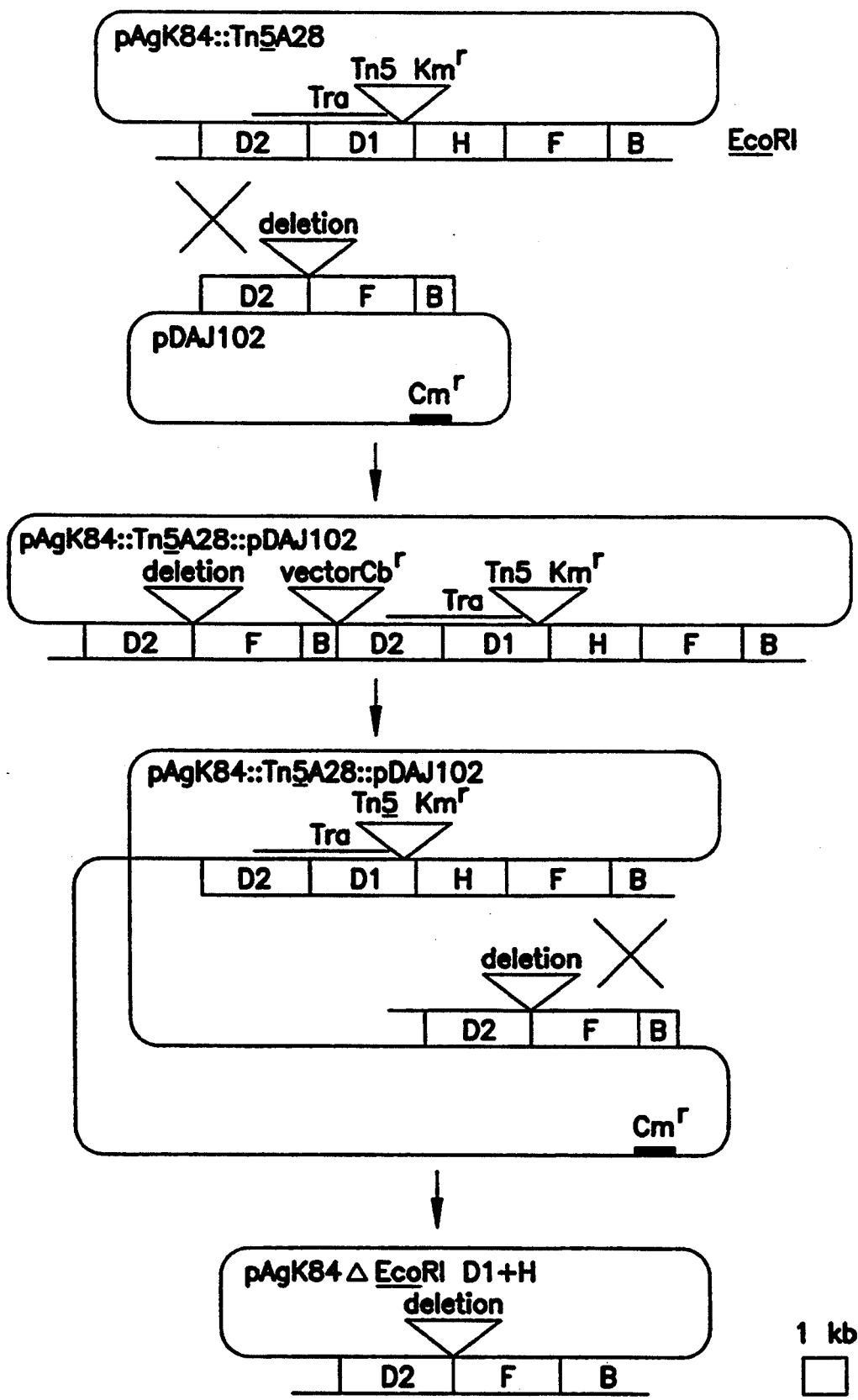

2. A non-pathogenic strain of *Agrobacterium radiobacter* K84 according to claim 1, wherein the plasmid has been further modified by deletion of the EcoRI H fragment as shown in FIG. 3.

3. A stable modified plasmid pAgK84 comprising genes encoding the synthesis of the antibiotic agrocin 84 and modified to prevent transfer by a deletion of the EcoRI D1 fragment which contains the transfer region to inhibit transfer of the plasmid.

4. A stable modified plasmid pAgK84 having a modification comprising a deletion of EcoRI fragments D1 and H of pAgK84 as shown in FIG. 3 to inhibit transfer of the plasmid.

* * * * *

UNITED STATES PATENT AND TRADEMARK OFFICE
CERTIFICATE OF CORRECTION

PATENT NO. : 5,354,684

DATED : October 11, 1994

INVENTOR(S) : Kerr et al.

It is certified that error appears in the above-identified patent and that said Letters Patent is hereby corrected as shown below:

Column 1, Line 9, "Agribacterium" should read --Agrobacterium--.

Column 1, Line 10, "utilising" should read --utilizing--.

Column 1, Line 14, "Agrobacteium" should read --Agrobacterium--.

Column 1, Line 22, "Aqrobacterium" should read --Agrobacterium--.

Column 1, Line 24, "antiobiotic" should read --antibiotic--.

Column 1, Line 48, "characterised" should read --characterized--.

Column 2, Line 4, "Aqrobacterium" should read --Agrobacterium--.

Column 2, Line 9, insert --was deposited on April 4, 1987 and-- after the word "which".

Column 2, Line 32, "characterised" should read --characterized--.

Column 2, Line 63, "antiobiotic" should read --antibiotic--.

Column 2, Line 65, "Aqrobacterium" should read --Agrobacterium--.

Column 3, Line 3, "mobilising" should read --mobilizing--.

Column 3, Line 14, "Agrobacerium radoiobacter" should read --Agrobacterium radiobacter--

Column 3, Line 27, delete "on" after the word "Apr.".

Column 3, Line 31, "utilised" should read -utilized--.

UNITED STATES PATENT AND TRADEMARK OFFICE
CERTIFICATE OF CORRECTION

PATENT NO. : 5,354,684

DATED : October 11, 1994

INVENTOR(S) : Kerr et al.

It is certified that error appears in the above-identified patent and that said Letters Patent is hereby corrected as shown below:

Column 3, Line 45, "radiocater" should read --radiobacter--.

Column 3, Line 67, "pagK84" should read --pAgK84--.

Column 6, Line 32, "mini-preparations" should read --minipreparations--.

Column 7, Line 25, "wre" should read --were--.

Column 7, Line 27, "methods" should read --Methods--.

Column 7, Line 54, "25C." should read --25°C.--.

Column 8, line 10, "seedling" should read --seedlings--.

Column 8, Line 40, "StatistiCal" should read --Statistical--.

Column 8, Line 44, "analysed" should read --analyzed--.

Column 8, Line 54, "4C" should read --4°C.--.

Column 8, Line 59, "25C." should read --25°C.--.

Column 8, Line 66, "4C" should read --4°C.--.

Column 9, Line 29, "time" should read --times--.

Column 9, Line 31, "aqrobacteria" should read --agrobacteria.--.

UNITED STATES PATENT AND TRADEMARK OFFICE
CERTIFICATE OF CORRECTION

PATENT NO.  :  5,354,684

DATED       :  October 11, 1994

INVENTOR(S) :  Kerr et al.

It is certified that error appears in the above-identified patent and that said Letters Patent is hereby corrected as shown below:

Column 9, Line 32, "Mini-preparations" should read --Minipreparations--

Column 9, Line 34, "characterised" should read --characterized--.

Column 9, Line 60, "analysed" should read --analyzed--.

Signed and Sealed this

Twelfth Day of December, 1995

Attest:

BRUCE LEHMAN

Attesting Officer

Commissioner of Patents and Trademarks